United States Patent [19]

Chamuel

[11] Patent Number: 4,481,821
[45] Date of Patent: Nov. 13, 1984

[54] ELECTRO-ELASTIC SELF-SCANNING CRACK DETECTOR

[75] Inventor: Jacques R. Chamuel, Framingham, Mass.

[73] Assignee: The Charles Stark Draper Laboratory, Inc., Cambridge, Mass.

[21] Appl. No.: 521,114

[22] Filed: Aug. 8, 1983

[51] Int. Cl.³ ............................................. G01N 29/04
[52] U.S. Cl. ....................................... 73/617; 73/643; 73/644
[58] Field of Search ................. 73/643, 609, 644, 617; 324/207, 222

[56] References Cited

U.S. PATENT DOCUMENTS

| 2,758,276 | 8/1956 | Foerster . | |
| 4,035,762 | 7/1977 | Chamuel | 73/339 A |
| 4,121,155 | 10/1978 | Chamuel | 324/207 |
| 4,144,519 | 3/1979 | Chamuel . | |
| 4,144,574 | 3/1979 | Chamuel | 324/208 |
| 4,216,352 | 8/1980 | Chamuel | 181/111 |
| 4,231,260 | 11/1980 | Chamuel | 73/597 |
| 4,385,634 | 5/1983 | Bowen | 73/643 |
| 4,430,897 | 2/1984 | Quate | 73/643 |

Primary Examiner—Howard A. Birmiel
Attorney, Agent, or Firm—Weingarten, Schurgin, Gagnebin & Hayes

[57] ABSTRACT

A contactless self-scanning electro-elastic nondestructive testing technique is described for determining in real time the presence, location, number and size of defects present on the surface of a material under test. In one embodiment the apparatus includes means for inducing eddy currents or current flow in the surface of the conductive material. A magnetostrictive delay line is disposed parallel to the direction of current flow and equidistant and in fixed spatial relation with the surface. The presence of a crack or defect in the surface proximate to the delay line creates transverse eddy currents or transverse currents in the material which interact locally with the magnetostrictive delay line to induce elastic waves in the delay line. The elastic waves are generated in the delay line only at locations corresponding to the edges of the defects. An ultrasonic sensor coupled to the delay line is used to detect the elastic waves travelling in the delay line. The location of a crack or fissure may be determined based on the time of arrival of the elastic waves at the sensor. The self-scanning line electro-elastic probe is not susceptible to the presence of elastic waves propagating in the material under test. The invention is applicable for inspection of flat and curved surfaces.

Another elastic wave transmitting medium may be employed in place of the magnetostrictive delay line given appropriate excitation means. Additionally, the delay line may be fabricated as a two-dimensional sheet with ultrasonic sensors disposed at selected locations on the sheet to achieve rapid inspection of an area for defects, the location of defects being determinable based upon the time of arrival of induced elastic waves at respective sensors.

19 Claims, 4 Drawing Figures

ELECTRO-ELASTIC SELF-SCANNING CRACK DETECTOR

FIELD OF THE INVENTION

This invention relates to apparatus and methods for detection of surface defects in conductive materials and more specifically to contactless self-scanning electro-elastic nondestructive testing techniques capable of rapid inspection of large surface areas to determine in real time the presence, location, number and size of defects present on the surface of a conductive material under test.

BACKGROUND OF THE INVENTION

It is often necessary to verify in real time the mechanical integrity of materials having large areas to assure satisfactory quality of an article or workpiece. It is especially important to assure integrity and quality in aircraft componentry where the failure of components may have life threatening consequences. In other applications, it is important to inspect or monitor the workpiece or member in real time even while the workpiece or member is subjected to stress.

Many non-destructive inspection techniques have been developed in the past. Eddy current inspection techniques, in particular, have been employed for a number of years for the inspection of materials having conductive surfaces, however, known eddy current probes have proved ineffective in differentiating the presence of multiple defects and sensing small surface defects below 0.010. One form of eddy current probe known in the art employs a coil which is scanned over the surface to be inspected. A defect in the surface, of sufficient size, causes a change in the electrical impedance of the coil. The probe produces an output signal indicative of defects proximate to the eddy current probe. An extremely small area coil is needed to permit detection of small defects. The prior art eddy current probes, even of small area, have not been effective in reliably detecting defects of less than 0.010 inches in length. Additionally, the use of eddy current coil probes requires the time consuming and inexacting process of X-Y scanning to complete inspection of a large area surface.

One eddy current defect sensor is disclosed a copending U.S. patent application of the same inventor and assignee as the present disclosure which is capable of detecting defects smaller than 0.010 inches. In this disclosure eddy currents are induced in a conductive workpiece by one or more wires disposed along a path parallel to a first axis, and defects are sensed with one or more wires disposed along a path perpendicular to and intersecting the first axis.

Another apparatus and method for eddy current detection of subsurface discontinuities in a conductive body is disclosed in U.S. Pat. No. 4,271,393 to Hansen, et al.

SUMMARY OF THE INVENTION

A method and apparatus are disclosed for rapid and efficient non-destructive inspection for cracks, fissures, or other defects of a large area workpiece having a surface of conductive material. A first wire is disposed parallel to and in fixed spatial relation with the surface of the workpiece. In one embodiment, a pulsed electrical current is passed through the wire and current flow through the wire induces eddy currents in the conductive surface parallel to the first wire. A magnetostrictive delay line, such as a nickel wire, is disposed closely parallel to the first wire and substantially equidistant from the surface of the workpiece. The presence of a defect or crack in the workpiece causes transverse eddy currents within the workpiece which magnetostrictively induce elastic waves in the delay line. The elastic waves travel in the magnetostrictive wire and are detected by an ultrasonic sensor. The location of the defect is determined by the time of arrival of the elastic wave at the ultrasonic sensor relative to the time of current pulse generation.

The defect detector operative in accordance with the present invention, may be manually scanned over the surface of a workpiece, automatically scanned over the surface of a workpiece, or the workpiece may be positioned with respect to the detector so as to effect full inspection of the full area of the workpiece surfaces. Additionally, the wires may be shaped to conform to a non-planar workpiece surface to permit inspection of such surfaces for defects.

In an alternative embodiment, pulsed currents are applied to the workpiece so as to flow along parallel paths directly through the workpiece. The presence of a defect produces transverse current components which electromagnetically couple elastic waves to a two-dimensional magnetostrictive delay line which is parallel to the workpiece surface being inspected. One or more ultrasonic sensors are disposed at selected locations of the delay line. Based on the time of arrival of elastic waves at each of the sensors with respect to current pulse energization of the workpiece, the precise location of surface defects is determinable.

DESCRIPTION OF THE DRAWINGS

The invention will be understood by reference to the following description in conjunction with the accompanying drawings in which.

DETAILED DESCRIPTION OF THE INVENTION

In accordance with the present invention, apparatus and method are disclosed that provide for detection and location of cracks, defects, or fissures in the surface of a conductive material, article, or workpiece. The apparatus includes means for applying electric current in the workpiece along a first axis or means for inducing an eddy current in the surface of the workpiece along a first axis and additionally includes a magnetostrictive delay line and an associated sensor coupled to transverse current electromagnetic fields resulting from at least one defect creating elastic waves in the magnetostrictive delay line.

Figure 1:
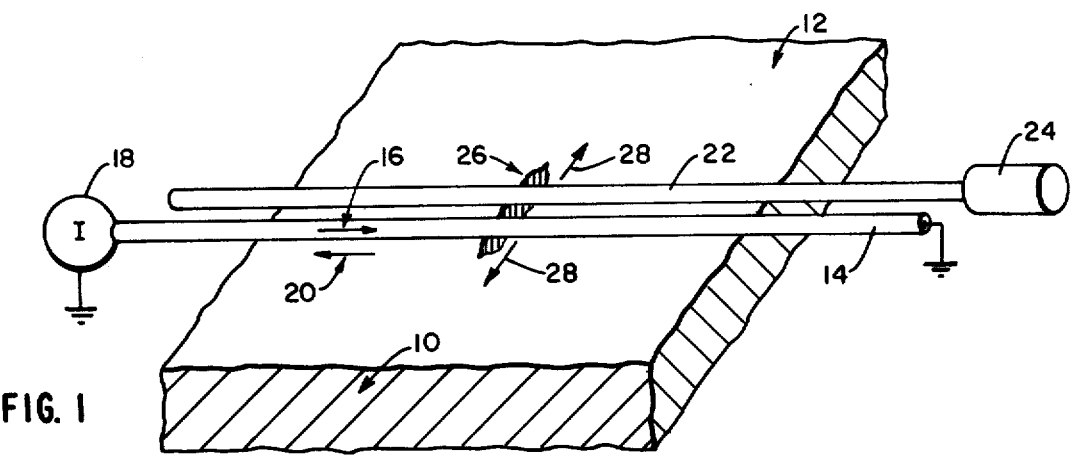
FIG. 1 is a pictorial representation of self-scanning line electro-elastic sensor in accordance with the present invention.

Referring to FIG. 1 there is shown a workpiece 10 having a surface 12 to be inspected. Parallel to the surface 12 is a first wire 14 which is disposed parallel to and in fixed spatial relation with the surface 12 of the workpiece 10. A pulsed current 16 produced by a source of current 18 flows through the wire 14. The flow of current 16 through the wire 14 results in an eddy current 20 in the surface 12 of the workpiece 10 parallel to the current 16 but of opposite direction as shown in FIG. 1. A magnetostrictive delay line 22, such as a nickel wire, is disposed parallel to the wire 14 and parallel to and substantially equidistant from the surface 12 of the workpiece 10. An ultrasonic sensor 24 is coupled to the magnetostrictive delay line 22 at one end. The sensor 24 is operative to produce an output signal representative of received elastic waves. The delay line 22 need only be magnetostrictive in the portion corresponding to surface area inspection. Details on a magnetostrictive delay line are shown in U.S. Pat. No. 4,035,762 of the same inventor.

A magnetic bias may be applied to the magnetostrictive delay line to enhance its sensitivity.

The presence of a defect 26 in the surface 12 to be inspected causes the pulsed eddy currents 20 to flow around the edges of the defect 26, thereby producing transverse eddy currents 28. The transverse pulsed currents 28 magnetostrictively induce an acoustic pulse in delay line 22 which travels as an elastic wave in the delay line 22. The elastic wave travels through the delay line 22 to the sensor 24 and the time of arrival of the elastic wave at the sensor 24 with respect to the time of application of current 16 by the source 18 is indicative of the location of the defect 26. In the embodiment shown in FIG. 1, the longer the time interval between application of current by the source 18 and receipt of the elastic wave by the sensor 24, the farther the defect 26 is located from the sensor 44. It is apparent that the sensor 24 may be coupled to either end of the magnetostrictive delay line 22.

Figure 2:
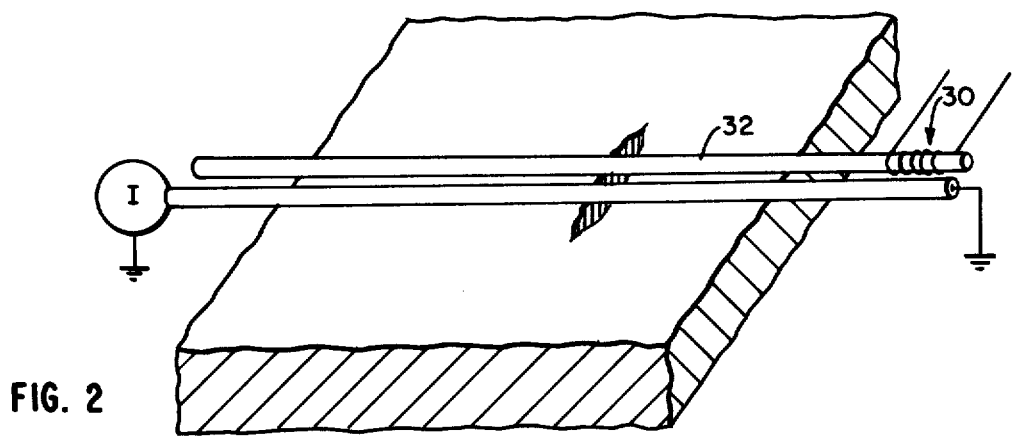
FIG. 2 is a pictorial representation of the sensor of FIG. 1 in which a coil is employed for sensing of elastic waves.

In the embodiment shown in FIG. 2, a coil 30 is employed as a sensor, and is disposed about the magnetostrictive delay line 32. The coil 30 is operative to produce an output signal by magnetostrictive interaction with an elastic wave travelling down the delay line 32 induced by a defect in the manner previously discussed.

Any form of ultrasonic sensor may be employed such as capacitive sensor, piezoelectric sensor, an optical sensor, or a fiber optic sensor. Additionally, the magnetostrictive delay line may be limited in length to the width of the surface to be inspected and the magnetostrictive delay line may be coupled to an elastic wave transmitting member which is in turn coupled to an ultrasonic sensor.

Figure 3:
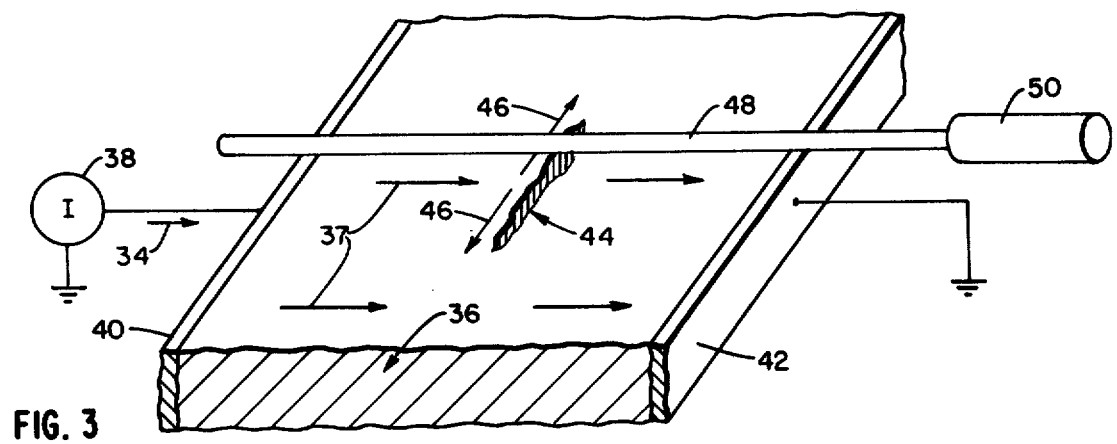
FIG. 3 is a pictorial representation of a sensor in accordance with the present invention in which currents are directly applied through a conductive workpiece.

In another embodiment illustrated in FIG. 3, pulsed currents 34 are applied directly to the workpiece 36 by a source of current 38. The current source is connected to a first electrode 40 which is disposed along a selected edge of the workpiece 36 and in conducting relationship therewith. A second electrode 42 is disposed along an opposing workpiece edge and provides a path for return current. The presence of a defect 44 causes transverse pulsed currents 46 resulting from the flow of current around the edges of the defect 44. The transverse pulsed currents produce in a magnetostrictive delay line 48 an elastic wave which travels along the the delay line 48. The elastic wave travels through the delay line 48 to an ultrasonic sensor 50 which is operative to provide an output signal representative of the received elastic waves. The presence and location of a defect in the surface of the workpiece may be determined based upon the time of arrival of an acoustic wave at the ultrasonic sensor 50.

The magnetostrictive delay line may be scanned with respect to the workpiece surface or the workpiece surface may be positioned with respect to the delay line to affect inspection of the entire workpiece surface. In the embodiment in which eddy currents in the workpiece are inductively coupled to a wire 14, the wire 14 is scanned along the workpiece with the delay line 22.

The surface to be inspected may be other than a flat surface in which case the magnetostrictive delay line and current carrying wire are shaped to the contour of the workpiece surface.

Figure 4:
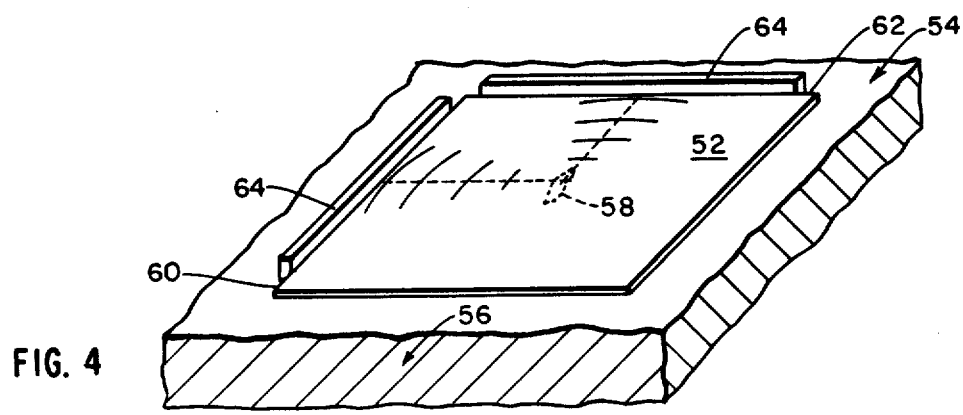
FIG. 4 is a pictorial representation of a two-dimensional magnetostrictive sheet employed as an acoustic delay line in accordance with the present invention.

A two-dimensional delay line may also be employed to map an area for defects as illustrated in FIG. 4. In this embodiment, a two dimensional sheet 52 is disposed proximate to and equidistant from the surface 54 of a conductive workpiece 56. The sheet 52 is presently shown to be a magnetostrictive sheet, such as nickel. A pulsed current is applied to the conductive workpiece 56 so as to produce discontinuities in the magnetic field resulting from current flow in the vicinity of defect 58 edges in workpiece 56 surface 54 in the manner previously described. Elastic waves are magnetostrictively generated in the sheet 52 at the defect locations, and the elastic waves travel through the sheet 52 to a first edge 50 and a second edge 62 of the sheet 52. Ultrasonic sensors 64 are disposed in elastic wave transmitting contact with the respective first and second edges of the sheet and are operative to produce output signals indicative of received elastic waves. The presence and location of defects in the workpiece 56 surface 54 may be determined based on the time of first arrival of the elastic waves at the sensors 64 disposed along first and second edges 60 and 62 of the sheet 52 with knowledge of the speed of sound in the sheet 52. The ultrasonic sensors 64 may be electromagnetically, mechanically, electrostatically, optically and magnetically coupled to the two-dimensional delay line producing an output signal indicative of travelling elastic waves.

Additionally, workpieces which are nonconductive but conductively plated may be inspected in accordance with the present invention by coupling to a single axis or two-dimensional acoustic delay line via electrostatic, optical or thermoelastic means. Examples of such workpieces include gold plated ceramic substrates.

The above described invention is illustrative of a novel method and apparatus permitting non-destructive inspection of a workpiece. Other modifications, embodiments, and departures from the present disclosure are possible without departing from the inventive concept contained herein. Consequently, the invention is to be viewed as embracing each and every novel feature and novel combination of features present in or possessed by the technique and apparatus herein disclosed and are limited solely by the scope and spirit of the appended claims.

What is claimed is:

1. Apparatus for sensing the presence and location of defects in a workpiece having a surface to be inspected comprising:

a medium capable of supporting travelling acoustic waves having at least one region adapted to couple to an acoustic sensor, said medium adapted to lie proximate, to a portion of said workpiece surface;

means for activating the workpiece simultaneously along said portion to cause generation of acoustic waves within said medium originating at locations proximate to irregularities in said portion of said workpiece;

at least one acoustic sensor coupled to said generated acoustic waves at said at least one of said medium regions, each of said sensors being operative to produce an output signal indicative of received acoustic waves;

the timing of output signal generation by each of said sensors with respect to workpiece activation being indicative of the presence and location of defects within said workpiece.

2. The apparatus of claim 1 wherein said medium is magnetostrictive and acoustic waves are electromagnetically induced in said medium proximate to a workpiece defect.

3. The apparatus of claim 1 wherein said medium is piezoelectric and acoustic waves are electromagnetically induced in said medium proximate to a workpiece defect.

4. The apparatus of claim 1 wherein said acoustic waves are induced in said medium by a thermal gradient proximate to a workpiece defect.

5. Apparatus for sensing the presence and location of a defect in a workpiece having a conductive surface comprising:

means for inducing a current pulse along a path in said workpiece;

a magnetostrictive delay line disposed generally parallel to said path in said workpiece;

the presence of a defect in said workpiece proximate to said delay line causing a travelling acoustic wave in said delay line;

an acoustic sensor coupled to said magnetostrictive delay line and operative to provide an output signal representative of an acoustic wave impinging said sensor;

said sensor output signal having characteristics indicative of defect presence and location.

6. The apparatus of claim 5 wherein said delay line is a nickel wire.

7. The apparatus of claim 5 wherein said acoustic sensor is a piezoelectric sensor.

8. The apparatus of claim 5 wherein said acoustic sensor is a capacitive sensor.

9. The apparatus of claim 5 wherein said acoustic sensor is an optical sensor.

10. The apparatus of claim 9 wherein said acoustic sensor is a fiber optic sensor.

11. The apparatus of claim 5 wherein said acoustic sensor is a coil and a magnetic bias disposed about said magnetostrictive delay line.

12. The apparatus of claim 5 wherein said means for inducing a current pulse in said workpiece surface includes:

a source of pulsed current;

a wire, electrically coupled to said source, and wire disposed parallel and proximate to said delay line and in a predetermined spatial relationship with said workpiece;

the flow of pulsed current through said wire producing an eddy current in said workpiece along said path.

13. The apparatus of claim 12 wherein said delay line is a nickel wire.

14. The apparatus of claim 5 wherein said means for inducing a current pulse in said workpiece includes:

a source of pulse current;

a first electrode electrically coupled to said source and contacting a first edge of said workpiece;

a second electrode electrically coupled to said source and providing a return current path, said second electrode contacting a second workpiece.

15. The apparatus of claim 14 wherein said delay line is a magnetostrictive wire.

16. The apparatus of claim 5 wherein said magnetostrictive delay line includes a magnetostrictive portion adjacent said workpiece surface to be inspected and a nonmagnetostrictive portion coupled at the end to said magnetostrictive portion opposite to said acoustic sensor.

17. The apparatus of claim 16 wherein said magnetostrictive portion is nickel.

18. A method for sensing the presence and location of defects in a surface of a workpiece to be inspected comprising the steps of:

locating a medium of acoustic wave transmitting material so as to lie proximate to a portion of said workpiece surface;

activating the workpiece simultaneously along said portion to cause generation of an acoustic wave within said medium originating at locations proximate to irregularities in said portion of said workpiece;

sensing the time of arrival with respect to the time of workpiece activation of acoustic waves at at least one sensing region of said medium;

determining the location of surface irregularities based upon the arrival times of elastic waves at each of said sensing regions with respect to the time of workpiece activation.

19. The method of claim 18 wherein said locating step comprises the step of locating a medium of magnetostrictive material proximate to a portion of said workpiece surface, and said activating step comprises the step of electromagnetically activating the workpiece by pulse current activation of said workpiece.

* * * * *